(12) United States Patent
Malik et al.

(10) Patent No.: US 9,057,568 B2
(45) Date of Patent: Jun. 16, 2015

(54) TEMPERATURE CONTROL DEVICES AND METHODS

(75) Inventors: Imran R. Malik, Pasadena, CA (US); Axel Scherer, Laguna Beach, CA (US)

(73) Assignee: CALIFORNIA INSTITUTE OF TECHNOLOGY, Pasadena, CA (US)

(*) Notice: Subject to any disclaimer, the term of this patent is extended or adjusted under 35 U.S.C. 154(b) by 521 days.

(21) Appl. No.: 12/638,829

(22) Filed: Dec. 15, 2009

(65) Prior Publication Data

US 2010/0152066 A1 Jun. 17, 2010

Related U.S. Application Data

(60) Provisional application No. 61/201,888, filed on Dec. 16, 2008, provisional application No. 61/201,841, filed on Dec. 16, 2008.

(51) Int. Cl.
| | |
|---|---|
| *F28F 13/00* | (2006.01) |
| *B01L 3/00* | (2006.01) |
| *B01L 7/00* | (2006.01) |
| *C12Q 1/68* | (2006.01) |
| *G01N 21/64* | (2006.01) |
| *F28D 21/00* | (2006.01) |

(52) U.S. Cl.
CPC ............... *F28F 13/00* (2013.01); *B01L 3/5027* (2013.01); *B01L 7/5255* (2013.01); *B01L 2200/147* (2013.01); *B01L 2300/0654* (2013.01); *B01L 2300/0829* (2013.01); *B01L 2300/1805* (2013.01); *B01L 2300/1883* (2013.01); *C12Q 1/6851* (2013.01); *F28D 2021/0077* (2013.01); *G01N 21/6428* (2013.01); *F28F 2013/008* (2013.01)

(58) Field of Classification Search
CPC ..... B01L 3/5027; B01L 7/5255; C12Q 1/6851; F28F 13/00; G01N 21/6428
USPC ............................................... 435/91.2, 287.2
See application file for complete search history.

(56) References Cited

U.S. PATENT DOCUMENTS

| | | | | |
|---|---|---|---|---|
| 4,281,708 A | * | 8/1981 | Wing et al. | 165/277 |
| 4,930,361 A | | 6/1990 | Nimberger | |
| 5,196,830 A | * | 3/1993 | Birging et al. | 340/584 |
| 5,272,518 A | | 12/1993 | Vincent | |
| 5,508,197 A | * | 4/1996 | Hansen et al. | 435/285.1 |
| 5,820,265 A | | 10/1998 | Kleinerman | |

(Continued)

FOREIGN PATENT DOCUMENTS

| | | |
|---|---|---|
| EP | 1972919 | 9/2008 |
| JP | 2002-139418 | 5/2002 |

(Continued)

OTHER PUBLICATIONS

PCT International Search Report issued for PCT Application No. PCT/US2010/039389 filed Jun. 21, 2010 in the name of California Institute of Technology et al.

(Continued)

*Primary Examiner* — Nathan Bowers
*Assistant Examiner* — Gautam Prakash
(74) *Attorney, Agent, or Firm* — Steinfl & Bruno LLP

(57) ABSTRACT

Temperature control devices and methods are described. The described temperature control devices and methods comprise optical emission and detection assemblies and can be used in PCR and qPCR applications.

16 Claims, 14 Drawing Sheets

(56) References Cited

U.S. PATENT DOCUMENTS

| | | | |
|---|---|---|---|
| 5,871,699 | A | 2/1999 | Ruggeri |
| 6,222,619 | B1 | 4/2001 | Herron et al. |
| 6,441,890 | B2 | 8/2002 | Wardlaw et al. |
| 6,623,696 | B1 | 9/2003 | Kim |
| 6,902,112 | B2 | 6/2005 | Sadler |
| 7,241,421 | B2 | 7/2007 | Webster et al. |
| 7,411,792 | B2 * | 8/2008 | Richards et al. ............ 361/704 |
| 7,564,541 | B2 | 7/2009 | Tuschel |
| 7,754,153 | B2 | 7/2010 | Miyamoto |
| 8,058,054 | B2 | 11/2011 | Owen et al. |
| 8,071,385 | B2 | 12/2011 | Haas et al. |
| 8,277,760 | B2 | 10/2012 | Letho |
| 8,395,773 | B2 | 3/2013 | Malik et al. |
| 2002/0046614 | A1 | 4/2002 | Alley |
| 2002/0160534 | A1 | 10/2002 | Herron et al. |
| 2003/0064507 | A1 | 4/2003 | Gallagher et al. |
| 2003/0109806 | A1 | 6/2003 | Weber et al. |
| 2004/0022677 | A1 | 2/2004 | Wohlstadter et al. |
| 2004/0091862 | A1 | 5/2004 | Brandenburg et al. |
| 2004/0152206 | A1 | 8/2004 | Davis et al. |
| 2005/0024636 | A1 | 2/2005 | Nakamura |
| 2005/0036142 | A1 | 2/2005 | Oldham et al. |
| 2005/0042651 | A1 | 2/2005 | Vann et al. |
| 2005/0059165 | A9 | 3/2005 | Davis et al. |
| 2005/0099621 | A1 | 5/2005 | Vez-Iravani et al. |
| 2005/0109396 | A1 | 5/2005 | Zucchelli et al. |
| 2005/0272142 | A1 | 12/2005 | Horita |
| 2005/0282266 | A1 | 12/2005 | Teng et al. |
| 2006/0186346 | A1 | 8/2006 | Wei |
| 2006/0199260 | A1 | 9/2006 | Zhang et al. |
| 2006/0211071 | A1 | 9/2006 | Andre et al. |
| 2006/0289787 | A1 | 12/2006 | Ohman et al. |
| 2006/0290934 | A1 | 12/2006 | Boekelman |
| 2007/0084279 | A1 * | 4/2007 | Huang et al. ............ 73/204.26 |
| 2007/0252090 | A1 * | 11/2007 | van de Water et al. ....... 250/429 |
| 2007/0272039 | A1 | 11/2007 | Hermet et al. |
| 2008/0003649 | A1 * | 1/2008 | Maltezos et al. ............ 435/91.2 |
| 2008/0176230 | A1 | 7/2008 | Owen et al. |
| 2008/0176755 | A1 | 7/2008 | Amundson et al. |
| 2008/0233011 | A1 | 9/2008 | Gundel et al. |
| 2009/0050209 | A1 * | 2/2009 | Rautavuori et al. ................ 137/2 |
| 2009/0176661 | A1 | 7/2009 | Harding et al. |
| 2010/0051124 | A1 | 3/2010 | Imran |
| 2010/0120164 | A1 | 5/2010 | Salafsky |
| 2010/0152066 | A1 | 6/2010 | Malik et al. |
| 2010/0192706 | A1 | 8/2010 | Fairs et al. |
| 2010/0291588 | A1 | 11/2010 | McDevitt et al. |
| 2010/0321696 | A1 | 12/2010 | Malik et al. |
| 2011/0104026 | A1 | 5/2011 | Yoon et al. |
| 2011/0132870 | A1 | 6/2011 | Moles |
| 2011/0151577 | A1 | 6/2011 | Zhang et al. |
| 2011/0207137 | A1 | 8/2011 | Malik et al. |
| 2011/0306120 | A1 | 12/2011 | Nicholls et al. |
| 2012/0003631 | A1 | 1/2012 | Yu et al. |
| 2012/0171759 | A1 | 7/2012 | Williams et al. |
| 2012/0180882 | A1 | 7/2012 | Malik et al. |
| 2013/0183659 | A1 | 7/2013 | Link et al. |

FOREIGN PATENT DOCUMENTS

| | | |
|---|---|---|
| JP | 2002-214225 | 7/2002 |
| JP | 2012-100549 | 5/2012 |
| WO | 00/21659 | 4/2000 |
| WO | 2007/102713 | 9/2007 |
| WO | 2011/005487 | 1/2011 |

OTHER PUBLICATIONS

PCT Written Opinion issued for PCT Application No. PCT/US2010/039389 filed Jun. 21, 2010 in the name of California Institute of Technology et al.
Non-Final Office Action issued for U.S. Appl. No. 12/820,104, filed Jun. 21, 2010 in the name of Imran R. Malik et al.; mailing date: Jun. 6, 2012.
Final Office Action issued for U.S. Appl. No. 12/820,104, filed Jun. 21, 2010 in the name of Imran R. Malik et al.; mailing date: Oct. 10, 2012.
Notice of Allowance issued for U.S. Appl. No. 12/820,104, filed Jun. 21, 2010 in the name of Imran R. Malik et al.; mailing date: Dec. 24, 2012.
PCT International Search Report mailed on Feb. 3, 2014 for PCT Application PCT/US2013/068170 filed on Nov. 1, 2013 in the name of California Institute of Technology.
PCT International Search Report mailed on Feb. 14, 2014 for PCT/US2013/068165 filed on Nov. 1, 2013 in the name of California Institute of Technology.
PCT Written Opinion mailed on Feb. 14, 2014 for PCT/US2013/068165 filed on Nov. 1, 2013 in the name of California Institute of Technology.
PCT International Search Report mailed on Feb. 5, 2014 for PCT/US2013/068172 filed on Nov. 1, 2013 in the name of California Institute of Technology.
PCT Written Opinion mailed on Feb. 5, 2014 for PCT/US2013/068172 filed on Nov. 1, 2013 in the name of California Institute of Technology.
Final Office Action mailed on Sep. 13, 2013 for U.S. Appl. No. 13/009,785, filed Jan. 19, 2011 in the name of Imran R. Malik et al.
Non-Final Office Action mailed on May 28, 2013 for U.S. Appl. No. 13/009,785, filed Jan. 19, 2011 in the name of Imran R. Malik et al.
Restriction Requirement mailed on Mar. 5, 2013 for U.S. Appl. No. 13/009,785, filed Jan. 19, 2011 in the name of Imran R. Malik et al.
Final Office Action mailed on Apr. 24, 2014 for U.S. Appl. No. 13/407,644, filed Feb. 28, 2012 in the name of Imran R. Malik et al.
Non-Final Office Action mailed on Nov. 26, 2013 for U.S. Appl. No. 13/407,644, filed Feb. 28, 2012 in the name of Imran R. Malik et al.
Restriction Requirement mailed on Sep. 17, 2013 for U.S. Appl. No. 13/407,644, filed Feb. 28, 2012 in the name of Imran R. Malik et al.
PCT Written Opinion mailed on Feb. 3, 2014 for PCT Application PCT/US2013/068170 filed on Nov. 1, 2013 in the name of California Institute of Technology.
PCT International Search Report mailed on Feb. 17, 2014 for PCT Application PCT/US2013/068171 filed on Nov. 1, 2013 in the name of California Institute of Technology.
Notice of Allowance mailed on May 14, 2014 for U.S. Appl. No. 13/947,469, filed Jul. 22, 2013 in the name of California Institute of Technology.
Notice of Allowance mailed on Feb. 28, 2014 for U.S. Appl. No. 13/947,469, filed Jul. 22, 2013 in the name of California Institute of Technology.
PCT Written Opinion mailed on Feb. 17, 2014 for PCT Application PCT/US2013/068171 filed on Nov. 1, 2013 in the name of California Institute of Technology.
PCT International Search Report mailed on Feb. 6, 2014 for PCT Application PCT/US2013/068173 filed on Nov. 1, 2013 in the name of California Institute of Technology.
PCT Written Opinion mailed on Feb. 6, 2014 for PCT Application PCT/US2013/068173 filed on Nov. 1, 2013 in the name of California Institute of Technology.
PCT International Search Report mailed on Oct. 16, 2013 for PCT Application PCT/US2013/051461 filed on Jul. 22, 2013 in the name of California Institute of Technology.
PCT Written Opinion mailed on Oct. 16, 2013 for PCT Application PCT/US2013/051461 filed on Jul. 22, 2013 in the name of California Institute of Technology.
PCT International Search Report mailed Feb. 17, 2014 for PCT Application PCT/US2013/068169 filed on Nov. 1, 2013 in the name of California Institute of Technology.
PCT Written Opinion mailed Feb. 17, 2014 for PCT Application PCT/US2013/068169 filed on Nov. 1, 2013 in the name of California Institute of Technology.
Rainina, El "Micro-fluidic (Lab-on-the-Chip) PCR Array Cartridge for Biological Screening in a Hand Held Device" *Final Report for CRADA No. 264. PNNL-T2-258-RU with CombiMatrix Corp* U.S. Department of Energy, Oct. 2010, 1.1-7.1.

(56) References Cited

OTHER PUBLICATIONS

Non-Final Office Action mailed on Sep. 17, 2014 for U.S. Appl. No. 13/009,785, filed Jan. 19, 2011 in the name of Imran R. Malik et al.
Notice of Allowance mailed on Jan. 7, 2015 for U.S. Appl. No. 13/009,785, filed Jan. 19, 2011 in the name of Imran R. Malik et al.
Restriction Requirement mailed on Jul. 7, 2014 for U.S. Appl. No. 13/336,717, filed Dec. 23, 2011 in the name of Imran R. Malik et al.
Non-Final Office Action mailed on Nov. 19, 2014 for U.S. Appl. No. 13/336,717, filed Dec. 23, 2011 in the name of Imran R. Malik et al.
Notice of Allowance mailed on Sep. 11, 2014 for U.S. Appl. No. 14/070,469, filed Nov. 1, 2013 in the name of Imran R. Malik et al.
Notice of Allowance mailed on Dec. 3, 2014 for U.S. Appl. No. 14/070,469, filed Nov. 1, 2013 in the name of Imran R. Malik et al.
Notice of Allowance mailed on Aug. 8, 2014 for U.S. Appl. No. 13/407,644, filed Feb. 28, 2012 in the name of Imran R. Malik et al.

* cited by examiner

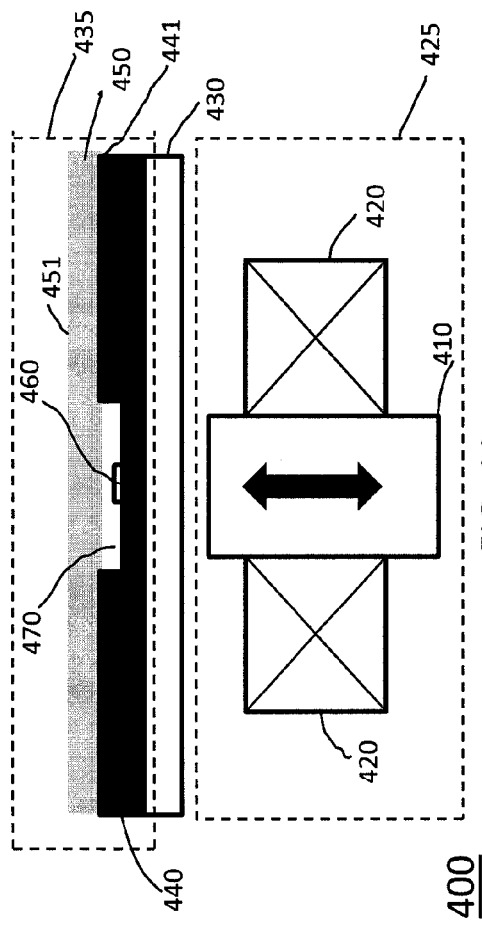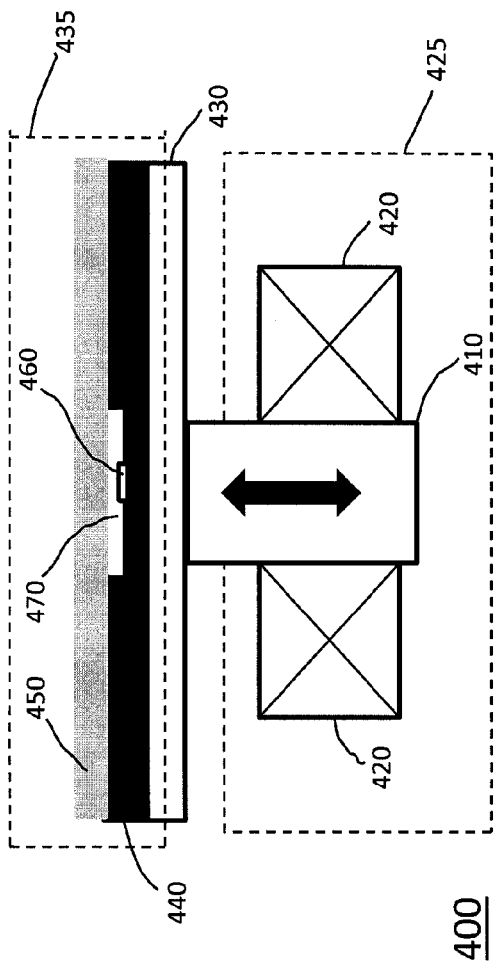

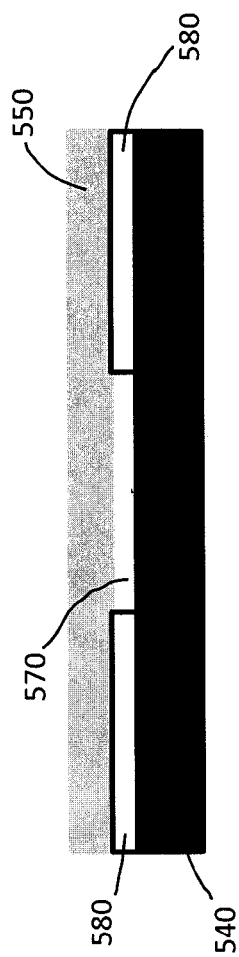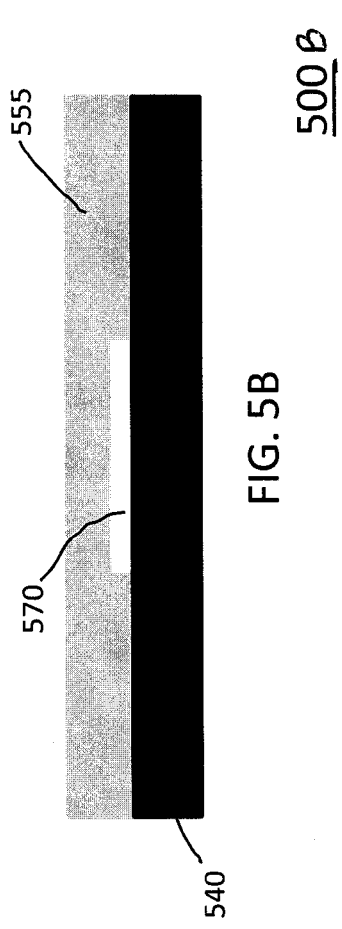

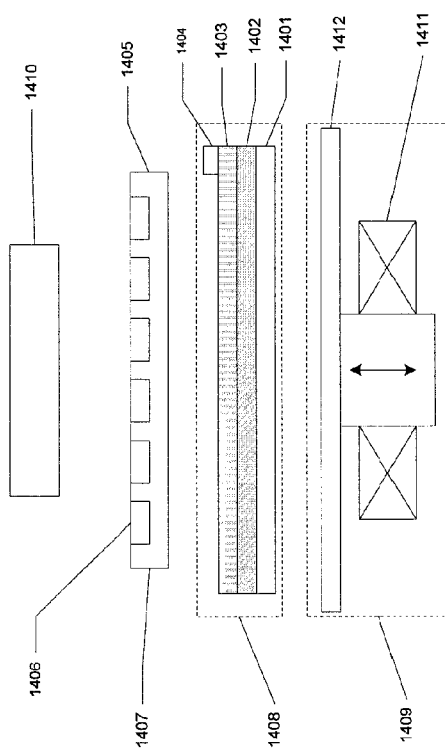
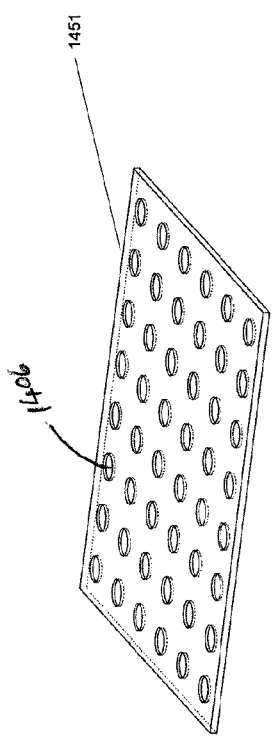
FIG. 11A
FIG. 11B

TEMPERATURE CONTROL DEVICES AND METHODS

CROSS REFERENCE TO RELATED APPLICATIONS

The present application claims priority to U.S. Prov. App. No. 61/201,888 and U.S. Prov. App. No. 61/201,841 both filed on Dec. 16, 2008 and which are incorporated herein by reference in their entirety.

FIELD

The present disclosure relates to temperature control. In particular, it relates to temperature control devices and methods.

BACKGROUND

There is a wide variety of scientific operations in which low-cost and accurate temperature control is involved and preferable.

An example of such operations is PCR (polymerase chain reaction). PCR is a technique used in molecular biology to amplify a portion of DNA (Deoxyribonucleic acid) or RNA (after reverse transcription to DNA). In a PCR reaction, the enzyme DNA polymerase generates copies of target sequence in an exponential fashion. Primers are used to amplify specific sequences and nucleotides are added as material which is assembled by polymerase to make DNA copies.

In order to obtain accurate results, rapid thermal cycling is used for fast PCR reactions. However, a time of reaction is typically limited by heating and cooling rates available in instruments. One of the fastest rates has been achieved by liquid flowing across a conducting substrate or a conductive material in contact with the substrate. However, this involves external pumps and complete liquid cooling and heating loops if the system is to be independent/portable. The fluid temperature is controlled accurately to a set point and this implies tight specifications of related control systems and therefore design complexities and higher costs.

Solutions based on Peltier coolers are expensive and power hungry. Systems using TEC's (thermo electric coolers) suffer from reliability issues. As a result of going through thousands of cycles, TEC's may suffer from damages that would make them non-functional.

There are instances where the instrumentation has to be robust, low power or prone to environmental stress like vibration etc. In this case designs similar to normal bench top instruments are not feasible. Complex designs for this purpose are difficult to adopt in a low cost setting like portable diagnostic equipment or Point of Care (POC) instruments.

SUMMARY

According to a first aspect, a temperature control method is provided, comprising: providing an object of interest at a first temperature; providing a thermal mass at a second temperature; providing a thermal contact having a first position and a second position; setting the thermal contact to the first position to establish a thermal connection between the object of interest and the thermal mass; establishing a desired temperature between the first temperature and the second temperature; and setting the thermal contact to the second position to break the thermal connection when the object of interest reaches the desired temperature.

According to a second aspect, a temperature cycling method is provided, comprising: providing an object of interest; providing a first thermal mass at a first temperature; providing a second thermal mass at a second temperature; providing a thermal contact having a first position and a second position; during a cycle, establishing a thermal connection between the object of interest and the first thermal mass by positioning the thermal contact into the first position; maintaining the thermal contact in the first position until the object of interest reaches a first desired temperature; the first desired temperature being between the first temperature and the second temperature; during the same cycle, establishing a thermal connection between the object of interest and the second thermal mass by positioning the thermal contact in the second position; maintaining the thermal contact in the second position until the object of interest reaches a second desired temperature, the second desired temperature being between the first temperature and the second temperature, and repeating the cycle.

According to a third aspect, a microfluidic thermal cycling system is provided, comprising: a microfluidic chamber; a heater; a thermal mass being moveable between a first position wherein thermal connection between the thermal mass and the microfluidic chamber is absent and a second position wherein the thermal mass is in thermal connection with the microfluidic chamber, wherein the system cycles between a first operative condition where the heater is on and the thermal mass is in the first position; and a second operative condition where the heater is off and the thermal mass is in the second position.

According to a fourth aspect, a qPCR system is provided, comprising: an optical emission assembly; an optical detection assembly, and the microfluidic thermal cycling system according to the third aspect, wherein during operation, the microfluidic chamber is illuminated by the optical emission assembly and a resulting generated fluorescent light is detected by the optical detection assembly.

According to a fifth aspect, multiple PCR reaction system is provided, comprising: a chip comprising a metal substrate; a heater; and an insulator, insulating electrically the metal substrate from the heater, a microarray assembly further comprising a plurality of wells; a thermal mass being moveable between a first position wherein thermal connection between the thermal mass and the chip is absent and a second position wherein the thermal mass is in thermal connection with the chip, wherein the system cycles between a first operative condition where the heater is on and the thermal mass is in the first position; and a second operative condition where the heater is off and the thermal mass is in the second position.

Further aspects of the present disclosure are shown in the descriptions, drawings and claims of the present application.

BRIEF DESCRIPTION OF FIGURES

FIGS. 4A-B show block diagrams of a microfluidic thermal cycling system with two different positionings of a thermal mass.

FIGS. 5A-D show four different embodiments of a microfluidic chamber according to an embodiment of the present disclosure.

FIG. 11A shows a multiple PCR reaction based system in accordance with an embodiment of the disclosure.

FIG. 11B shows an implementation of a microarray.

DETAILED DESCRIPTION

Herein, methods and devices for temperature control are described.

Figure 1:
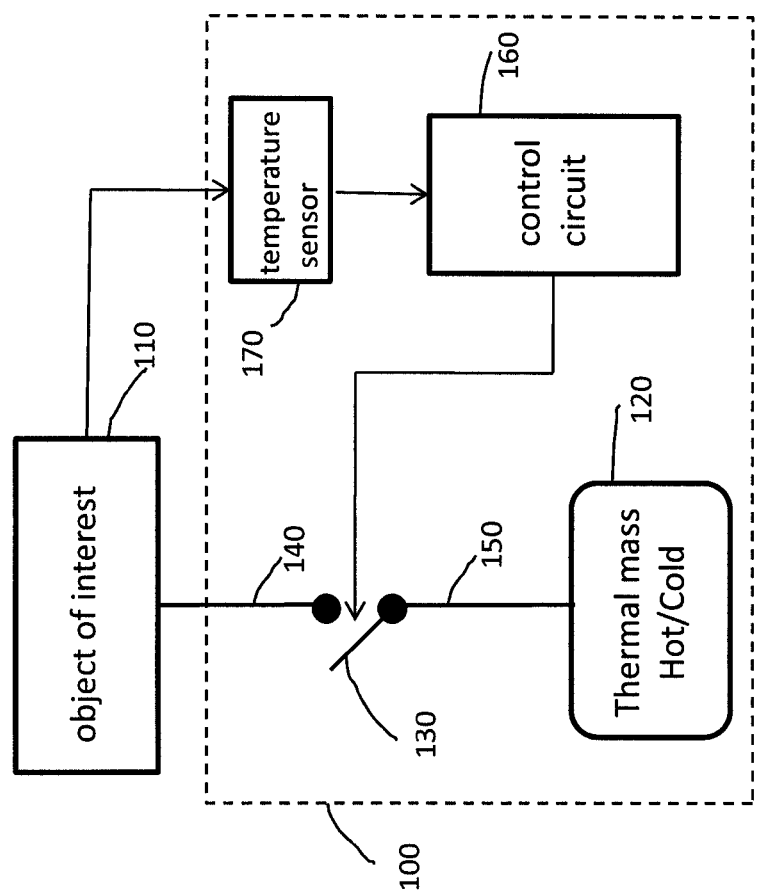
FIG. 1 shows a conceptual block diagram wherein an object of interest is connected with a thermal control system in accordance with an embodiment of the present disclosure.

FIG. 1 shows a conceptual block diagram where an object of interest (110) is connected with a temperature control system (100) according to an embodiment of the present disclosure. The temperature control system (100) comprises a thermal mass (120), a control circuit (160), a temperature sensor (170), a thermal contact (130) and two thermal paths (140, 150). As described later, a combination of the temperature sensor (170) and the control circuit (160) serves as a feedback control system. Throughout this document, an object of interest is defined as an object the temperature of which is to be measured and a thermal mass is defined as an object with appropriate thermal capacity.

Referring to FIG. 1, For the sake of description, it will be assumed that the object of interest (110) and the thermal mass (120) are respectively at temperatures $T_1$ and $T_2$. Moreover, it will be assumed that a temperature of the object of interest (110) is to be controlled to a target temperature Tc. According to an embodiment of the disclosure, the temperature $T_1$ can be larger or smaller than the temperature $T_2$ and the temperature Tc is between the temperatures $T_1$ and $T_2$. Further referring to FIG. 1, the temperature sensor (170) estimates the temperature of the object of interest (110) and provides an input to the control circuit (160) accordingly. Based on the input received from the temperature sensor (170), the control circuit (160) configures the thermal contact (130) in an open, closed or modified position.

As shown in FIG. 1, when the thermal contact (130) is in the closed position, a thermal connection is made from the object of interest (110) to the thermal mass (120) through the thermal paths (140, 150) and the thermal contact (130). Non-fluidic designs with very fast rates are possible. By way of example and not of limitation, it is assumed that $T_1 > T_c > T_2$. Based on this example, when the thermal contact (130) is in closed position, heat flows from the object of interest (110) to the thermal mass (120) and as a result, the temperature of the object of interest (110) start decreasing until it reaches the target temperature $T_c$. The thermal contact (130) is then set to the open position by the control circuit (160) through the mechanism described in the previous paragraph in reference to the temperature sensor (170) and the control circuit (160). The person skilled in the art will appreciate that, following the same example, as long as the temperature $T_2$ is less than $T_c$, no accurate measurement of $T_2$ is involved for proper functioning of the temperature control system (100). As described later and further continuing with the same example, the lower the temperature $T_2$, the faster the time to for the object of interest (110) to reach the target temperature $T_c$.

Further referring to FIG. 1, it is noted that the object of interest (110) may contain a substrate and/or other elements in contact with a core object, the temperature of which is to be measured. For example, for a PCR reaction the core object will be a PCR mix, but portions or all of a container, substrate or connecting elements can be regarded as the object of interest (110).

Figure 2:
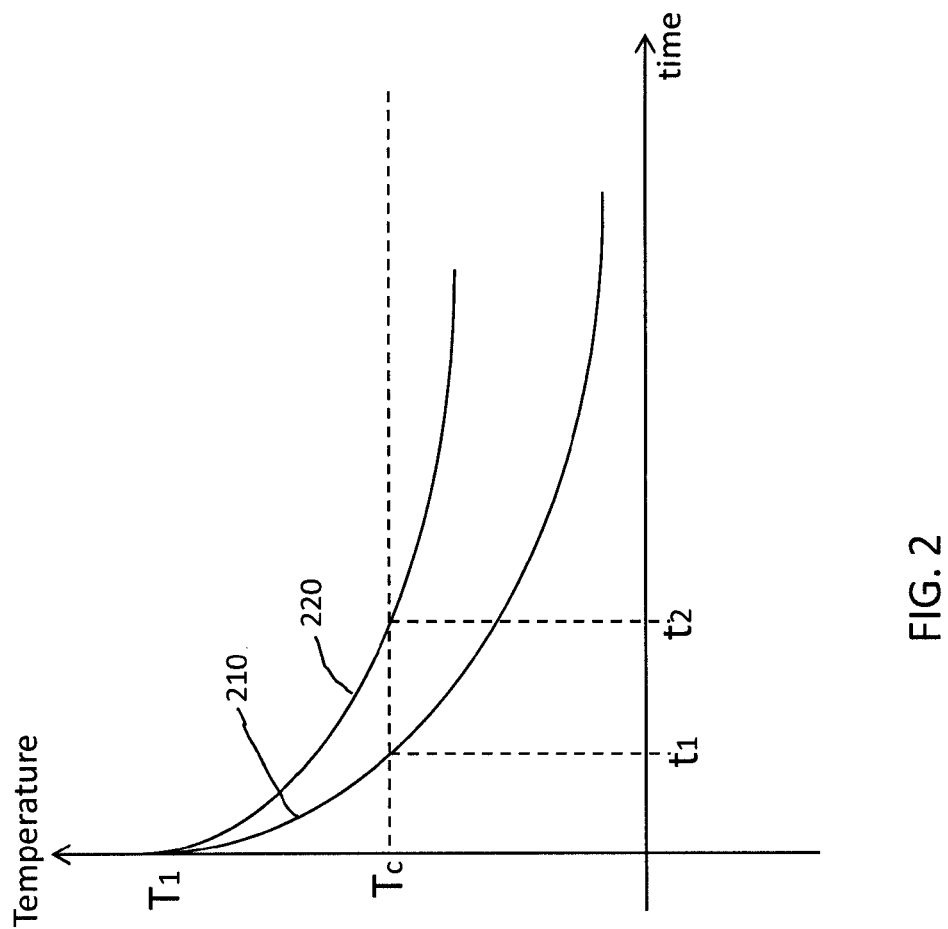
FIG. 2 shows two curves representing variations of the object of interest's temperature as a function of time for two different values of temperature of thermal mass

FIG. 2 shows two curves (210, 220) representing variations of the object of interest (110) temperature as a function of time. The curves (210) and (220) correspond respectively to the scenarios where the thermal mass (120) is at temperatures $T_2$ and $T_2'$ where $T_2' > T_2$. As can be seen from FIG. 2, the object of interest (110) of FIG. 1 takes a time $t_1$ to reach the target temperature Tc from the temperature $T_1$ when the thermal mass (120) of FIG. 1 is at temperature $T_2$. Referring to FIG. 1, when the thermal mass (120) is at temperature $T_2'$, it takes a time $t_2 > t_1$ for the object of interest (110) to reach the target temperature Tc from the same temperature $T_1$. In other words, a greater temperature gradient allows for faster heat transfer. This allows for larger operational ranges on the temperature of the thermal mass (120) of FIG. 1 which in turn results in an easier and more cost effective design of the temperature control system (100) shown in FIG. 1.

Referring to FIG. 1 and based on the discussion above, the person skilled in the art will appreciate that the thermal mass can be an object at some range of temperature to/from which some form of heat flow occurs. As an example, for applications where Tc is higher than the environment temperature, a container containing water at environment temperature is sufficient for the purpose of heat transfer from the object of interest being at a temperature $T_1 > Tc$. According to an embodiment of the disclosure, the temperature $T_2$ is above/below the target temperature Tc, depending on a desired direction of heat transfer. In other words, the thermal mass (120) can be at a variable temperature or within a range of temperatures where accurate temperature measurement is not involved.

Further referring to FIG. 1, according to various embodiments of the present disclosure, different existing components can be used to make the thermal contact (130). Some components which are not initially designed/meant for this purpose can work as well. For example, a mechanical contact in an electric switch which can be used as a thermal contact without involving any electric current. Following is a partial list of existing components used in various embodiments of the present disclosure to form the thermal contact (130):

Relays
    Electromechanical Relays—all types
    Relay (solid-solid)
    Mercury relay
    Vacuum relay
    Mercury wetted relay
Contactor
Electrical switch
MEMS switches—electrostatic, electromagnetic, pneumatic etc
Actuator based contact which can use following actuation
    SMA (Shape Memory Alloys)
    Electromagnetic
    Electrostatic
Manual
Gravity assisted contacts
Liquid metal—solid contact Modifications to contacts
  CNT coated
  Nano-structured to improve performance/increase contact area
  Latched
  Sliding
  Liquid Flow
  Variable pressure, distance
Custom types
  A syringe filled with liquid metal. When the plunger goes forward contact is made, when the plunger moves away, there is no contact.
  Patterned/grooved metal contacts to increase contact area
  Sliding metal surfaces with or without wetting
  Controllable contact area, pressure and distance
Radiation Assisted/Controlled
  If one body is at a very different temperature, changing distance or blocking radiation by a screen can help in heat transfer. Note that this allows heat transfer without mechanical contact.
Convection Assisted/Controlled
  The heat transfer rate can be controlled by changed convection distance or opening or closing some channel for fluid flow.

Referring to FIG. 1, various embodiments with different rates of heat transfer from the object of interest (110) to the thermal mass (120) can be envisaged. For example, modifying the distance between the thermal contact (130) and the thermal path (140) can provide variable radiation and convection heat transfer. In a further example, by modifying pressure against a contact area between the thermal contact (130) and the thermal path (140), the heat transfer rate can be controlled.

According to an embodiment of the present disclosure, coating of contact areas is used to improve heat transfer rate. As a result of coating, smaller contact areas can be used for the same heat transfer rates. Examples of coating are CNT coating (carbon nano-tube), or using flexible graphite, mercury, metal foils and Gallium.

Further referring to FIG. 1, according to other embodiments of the present disclosure, a heater/TEC is used to heat/cool the thermal mass (120) in order to set the thermal mass (120) to a desired temperature. Such embodiments benefit from a thermal mass of the heater/TEC to achieve an even faster heat transfer. In such embodiments, when used in temperature cycling applications, the heater/TEC does not undergo through temperature cycling and is only used for setting a temperature for the thermal mass (120). As such, better reliability is achieved with these embodiments compared for example with conventional temperature cycling systems where TEC's are also going through temperature cycling and therefore suffer from potential damage after few thousands of cycles. Furthermore, less power is consumed as the mass of TEC is not undergoing temperature cycling.

With continued reference to FIG. 1, according to a further embodiment of the disclosure, the thermal contact (130) is a latching type relay. Latching type relays do not consume power while latched in a position. As a result, power is consumed only during switching of the thermal contact (130) and reading the temperature of the object of interest (110) by the temperature sensor (170). Moreover, latches can be added in design for linear or rotary actuator based contacts like solenoids.

Figure 3:
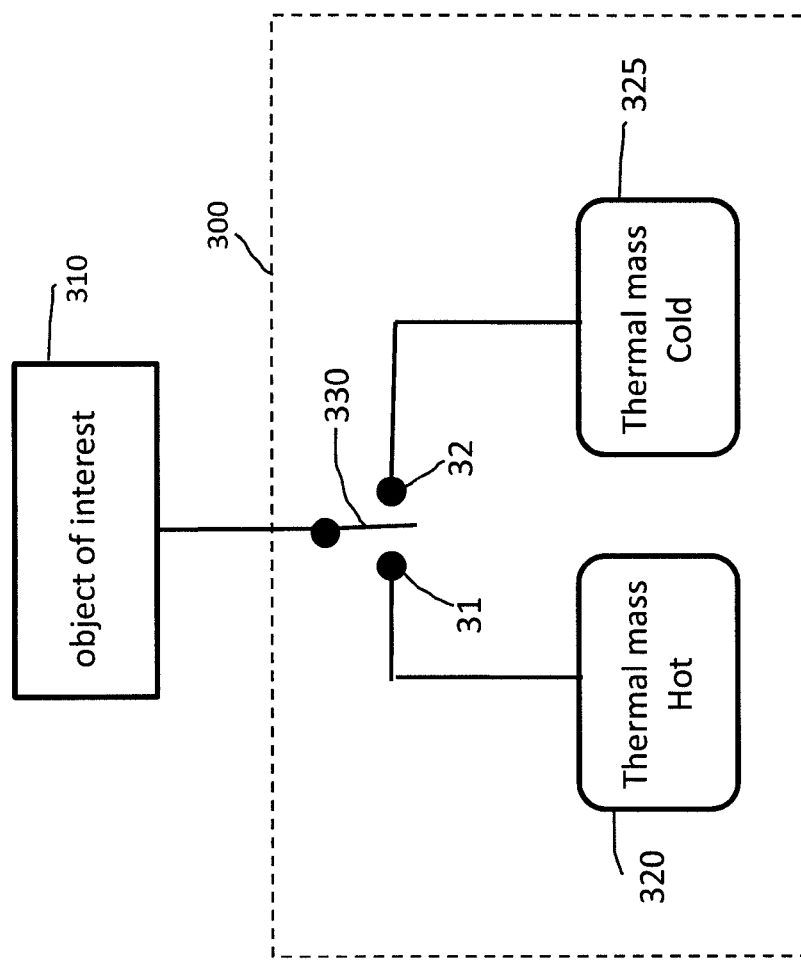
FIG. 3 shows an object of interest connected with a thermal cycling system according to an embodiment of the present disclosure.

FIG. 3 shows an object of interest (310) connected with a thermal cycling system (300) in accordance with an embodiment of the present disclosure. The thermal cycling system (300) comprises a hot thermal mass (320) being at a temperature $T_1$, a cold thermal mass (325) being at a temperature $T_2$ and a thermal contact (330). The thermal contact (330) switches between two positions (31, 32). The thermal contact (330) can be controlled using a control system (not shown) in a similar way as described previously with reference to FIG. 1 or manually. By switching the thermal contact (330) between the two positions (31, 32), the object of interest (310) undergoes a temperature cycling between a hot temperature Thot and a cold temperature Tcold. According to an embodiment of the disclosure, the temperatures Thot and Tcold are in between the temperatures $T_1$ and $T_2$.

Referring to FIG. 3, according to an embodiment of the disclosure, thermal cycling is achieved without consuming any power. In such embodiment, a mercury thermometer (not shown) can be used to measure a temperature of the object of interest (310). A manual electrical switch or just a metal contact/wire/plug can be used in the same embodiment to build the thermal switch (330). Further referring to FIG. 3, according to the same embodiment, the hot thermal mass (320) and the cold thermal mass (325) can respectively be a container of hot water and a container with ice. Such embodiment is very useful in some areas where cold/hot source like water can be found or in conflict situations or after natural disasters where power infrastructure becomes unavailable.

The person skilled in the art will understand that various other embodiments wherein multiple switches or switch configurations like SPDT (Single Pole Double Throw) switches are used can be envisaged. In such embodiments, a convenient number of switches and thermal masses at different temperatures are used and an object of interest is cycled through several distinct temperatures.

In what follows, embodiments according to the present disclosure that are usable in PCR applications are described.

FIG. 4A shows a block diagram of a microfluidic thermal cycling system (400) in accordance with an embodiment of the present disclosure. The microfluidic thermal cycling system (400) comprises a moving system (425), a heater (430), and a PCR chamber (435) attached to the heater (430) as shown in FIG. 4A. The moving system (425) further comprises a movable thermal mass (410) and a solenoid (420). The PCR chamber (435) comprises in turn, a substrate (440), a microfluidic reservoir (470) and a transparent cover (450). The microfluidic reservoir (470) can be lithographically defined to provide a channel for a fluid to flow. In other words, the substrate (440) is embossed, etched, milled or machined to define the microfluidic reservoir (470) where a PCR mixture is held. According to an embodiment of the disclosure, the transparent cover (450) is bonded or glued to the substrate (440).

Referring to FIG. 4A, according to a further embodiment of the disclosure, the substrate (440) is made of metal (e.g., aluminum or copper). A temperature sensor (460) is also shown in FIG. 4A. The temperature sensor (460) is used to measure a temperature of the fluid inside the microfluidic reservoir (470). According to a further embodiment of the disclosure, the temperature sensor can also be located outside the microfluidic reservoir (470) as described later.

According to an embodiment of the present disclosure, the thermal cycling system (400) is designed based on resistive heating and contact cooling wherein the heater (430) is a thin film heater. Further embodiments can also be envisaged where the heater is on a top side (441) of the heater (440) or the heater (440) is transparent (e.g., ITO heaters) and located on a top side of the PCR chamber (435). As shown in FIG. 4A, a PCR mixture held in the PCR chamber (435) experiences two different temperatures Thot and Tcold (Thot>Tcold) in a temperature cycle. During the temperature cycle, the heater (430) is turned on to increase the PCR mixture temperature. When the PCR mixture reaches Thot, the heater (430) is turned off and the solenoid (420) is activated to move the movable thermal mass (410) towards the microfluidic chamber (435). As a consequence, a thermal connection is made between the movable thermal mass (410) and the microfluidic chamber (435) through the heater (430), as shown in FIG. 4B. In this way, heat is transferred from the PCR chamber (435) to the thermal mass (410). As a result, the PCR mixture temperature starts dropping until it reaches Tcold after which, the solenoid (420) is reactivated such that this time the movable thermal mass (410) detached from the heater (430) and moves back to an original position where there is no thermal connection between the thermal mass (410) and the microfluidic chamber (435). By turning the heater (430) on again, the microfluidic chamber (435) temperature starts rising again and a new cycle commences. The person skilled in the art will understand that PCR protocols with more than two temperatures can also be handled in a similar way as described. The person skilled in the art will also understand that control strategies can be employed while heating and cooling. For example PID control can be used to drive the heater (430).

Further referring to FIGS. 4A-B, according to an embodiment of the present disclosure, controlling a function of the heater (430) and the solenoid (420) is performed using a control system (not shown) the function of which is substantially similar to what was described in reference to the control circuit (160) and the temperature sensor (170) of FIG. 1.

With continued reference to FIGS. 4A-B, according to an embodiment of the disclosure, in order to reduce a thermal resistance between the fluid and the heater (430) as well as a thermal resistance between the fluid and the movable thermal mass (410), the substrate (440) is made substantially flat but wide using metal (e.g., copper or aluminum). As a result, PCR amplification speed is increased. In one case the thickness of the fluid in the reservoir is 100 micrometer while the volume of the reaction is 10 microliter.

Figure 5C:
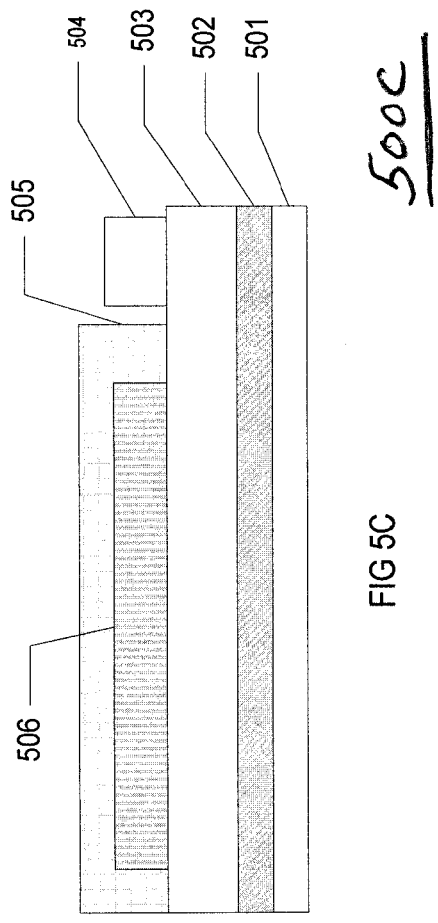

FIGS. 5A-D show various embodiments according to the present disclosure for a PCR chamber (500A-D). The embodiment shown in FIG. 5A is a bonded three-layer device comprising a polymer spacer layer (580) sandwiched between a transparent cover (550) and a metal substrate (540). According to an embodiment of the disclosure, PCR-compatible adhesive can be used for bonding different layers.

In the embodiment shown in FIG. 5B, a transparent cover (555) is patterned to define the microfluidic reservoir (570). According to an embodiment of the present disclosure, the transparent cover (555) is a made of a polymer.

In the embodiment shown in FIG. 5C, a temperature sensor (504) is provided on a metal substrate (503). An electrical insulator (502) is electrically insulating the metal substrate (503) from a heater film (501).

Figure 5D:
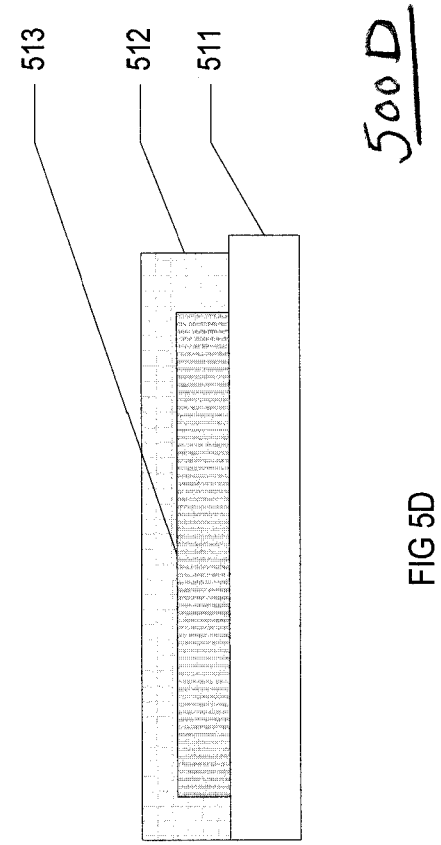

The embodiment shown in FIG. 5D is similar to the embodiment of FIG. 5B except that a heater and a temperature sensor (not shown) are integrated within the PCR chamber (500D) and thus making it less expensive and simpler.

In accordance with a further embodiment of the disclosure, a temperature can be sensed by the change in a resistance of a heater. Since materials have positive or negative temperature coefficients, temperature can be measured by estimation of resistance. Resistance can be detected by various methods. As an example, in time multiplexing the temperature is detected by passing a low current during times when heater in not ON. Current can be measured when the heater is ON to estimate resistance. Alternatively, an alternating current and voltage signal can be superimposed on a heating signal to estimate the resistance at all times.

Figure 6A:
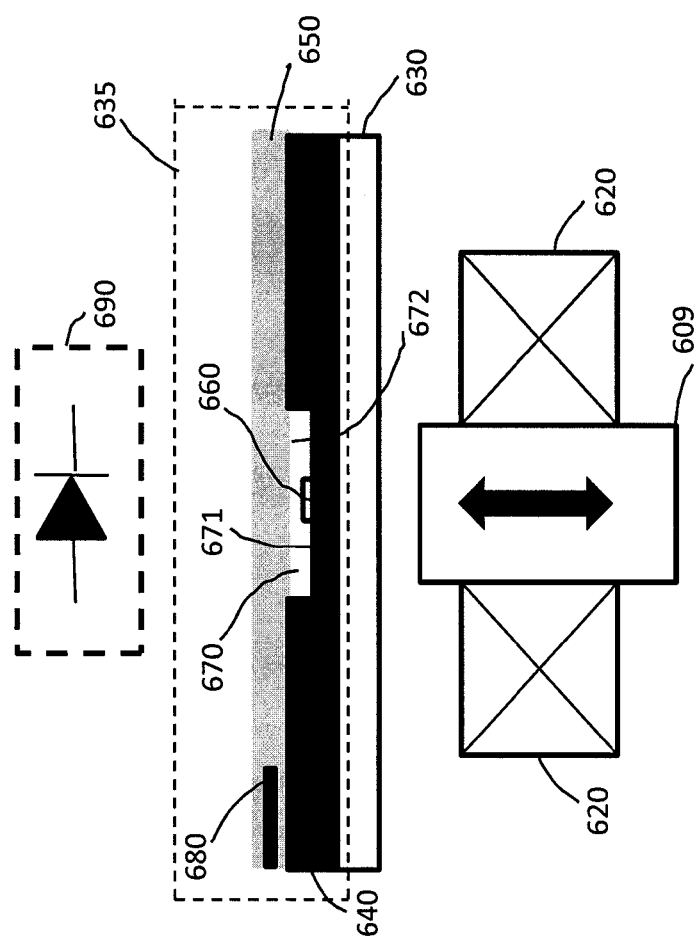
FIGS. 6A-B shows qPCR systems in accordance with embodiments of the present disclosure.

FIG. 6 shows a qPCR system (600A) in accordance with an embodiment of the present disclosure. qPCR (quantitative real time polymerase chain reaction) or kinetic polymerase chain reaction is a technique which allows quantification of DNA amplification during the PCR reaction instead of at the end. It can use non-specific dyes/reporter molecules (fluorescent, electrochemical or other) or sequence specific DNA probes with reporter (fluorescent, electrical or other)

As shown in FIG. 6, the qPCR system (600A) comprises a PCR chamber (635). Similarly to the PCR chamber (435) of FIG. 4A, the PCR chamber (635) shown in FIG. 6 comprises a substrate (640), a microfluidic reservoir (670), a transparent cover (650) and a temperature sensor (660) used to measure a PCR mixture temperature. Differently from the PCR chamber (435) of FIG. 4A, the PCR chamber (635) shown in FIG. 6 comprises a light source (680) integrated in the transparent cover (650). Also, in a similar manner as described above in reference to the microfluidic thermal cycling system (400) of FIG. 4, the qPCR system (600) further comprises a solenoid (620), a movable thermal mass (609) and a heater (630).

Referring to FIG. 6, the light source (680) illuminates the PCR chamber (635) for fluorescence measurements during thermal cycling. Fluorescence is collected by a fluorescence photo-detector (690) located above the PCR chamber (635). According to an embodiment of the disclosure, the fluorescence photo-detector (690) is a silicon p-n diode detector. The approach adopted here, is to integrate already existing components from consumer electronic devices to construct a cost-effective, rugged and fast (e.g., thirty cycles in less than five minutes) real-time qPCR system. Another goal is to integrate as much of a device onto a single substrate to minimize problems with mechanical misalignment of the qPCR system. According to an embodiment of the disclosure, the light source (680) is an in-plane LED source which is commonly used for light guiding systems in cell-phones.

Figure 6B:
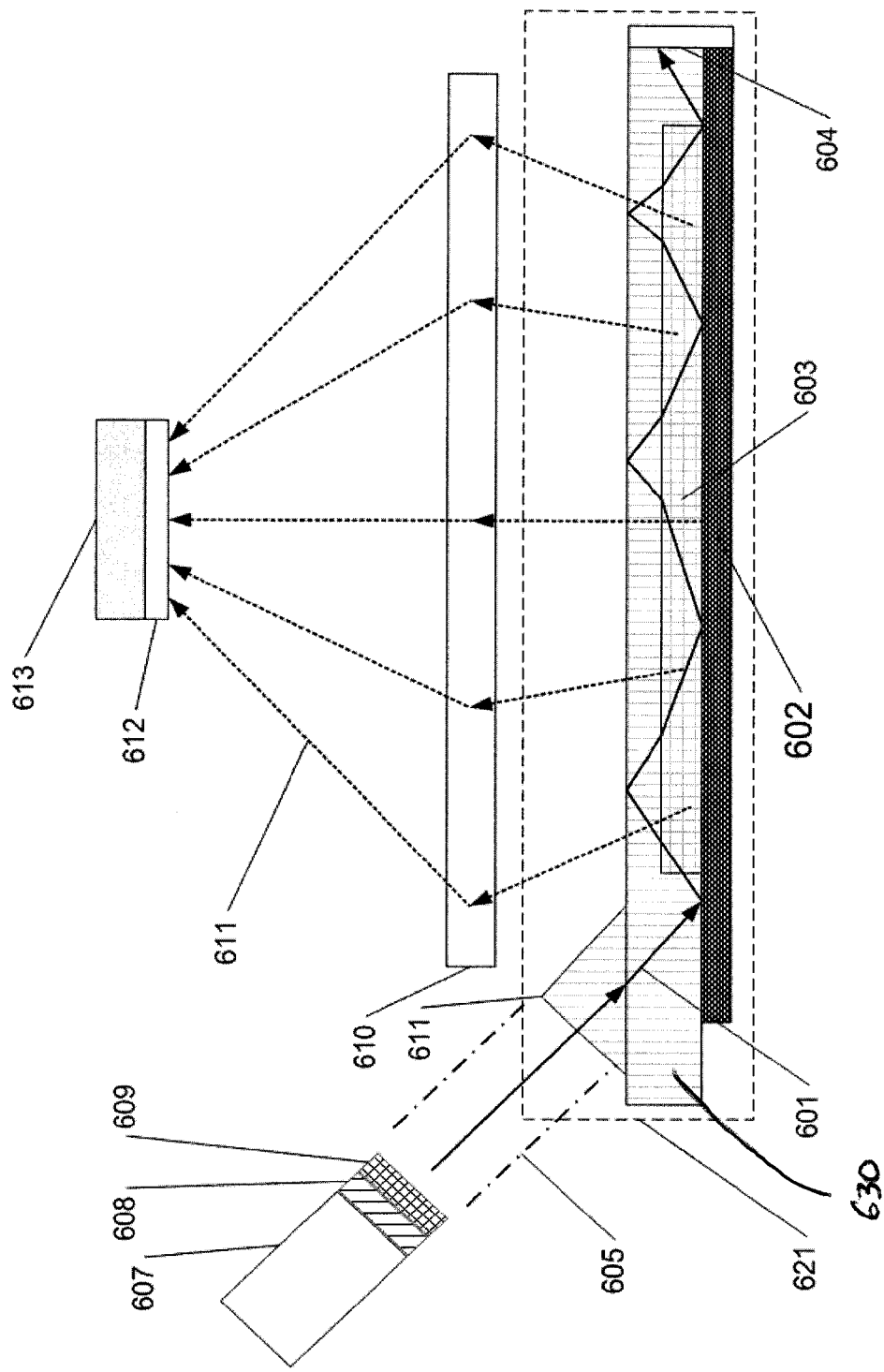

FIG. 6B shows a qPCR device (600B) in accordance with an embodiment of the present disclosure. A light source (607) is shown in FIG. 6B. Differently from the embodiment of FIG. 6A, the light source (607) is located outside a PCR chamber (621). According to an embodiment of the disclosure, the light source (607) is an LED. A lens (608) and excitation filter (609) are also shown in FIG. 6B. The excitation filter (609) is used to filter light. Further shown in FIG. 6B is a coupling prism (611). The coupling prism (611) is used to couple light into the PCR chamber (621) at a certain angle. According to an embodiment of the disclosure, there is a range of angles for which light will pass through a PCR fluid within a microfluidic reservoir (603). A light outside that range of angles will stay inside a polymer (630) since the refractive index of the polymer (630) is higher than that of the PCR fluid. Thus excitation rays (601) stay inside the PCR chamber (621) and illuminate a the PCR fluid within the microfluidic reservoir (603). A reflector (604) is placed at one side of the chip (621) to let the light reflect back and to be used again. A light guide (605) is also shown in FIG. 6B. The light guide (605) is used to get light at a particular angle as well as to diffuse and transport the light into the PCR chamber (621). Also shown in FIG. 6B, is an emission filter (612) which is used to filter out any portion of excitation. The qPCR device (600B) further comprises an optical structure (610). The optical structure (610) is used to capture fluorescent light and guide it to a detector (613). Other embodiments can be envisaged wherein the light source (607) can also be coupled from the side and therefore no coupling prism is used. The coupling prism (611) can be an integral part of the PCR chamber (621) or be a part of the light guide (605) separate from the PCR chamber (621).

PCR systems may experience thermal overshoot during operation. Avoiding thermal overshoot and reducing temperature stabilization time during thermal cycling, results in constant sample temperatures which are beneficial for PCR operation. Referring to FIG. 6, by reducing a vertical distance between a bottom (672) of the transparent cover (650) and a top (671) of the substrate (640), the heat transfer rate to all parts of the PCR mixture within the microfluidic reservoir (670) is increased and therefore temperature stabilization time is decreased.

Figure 7:
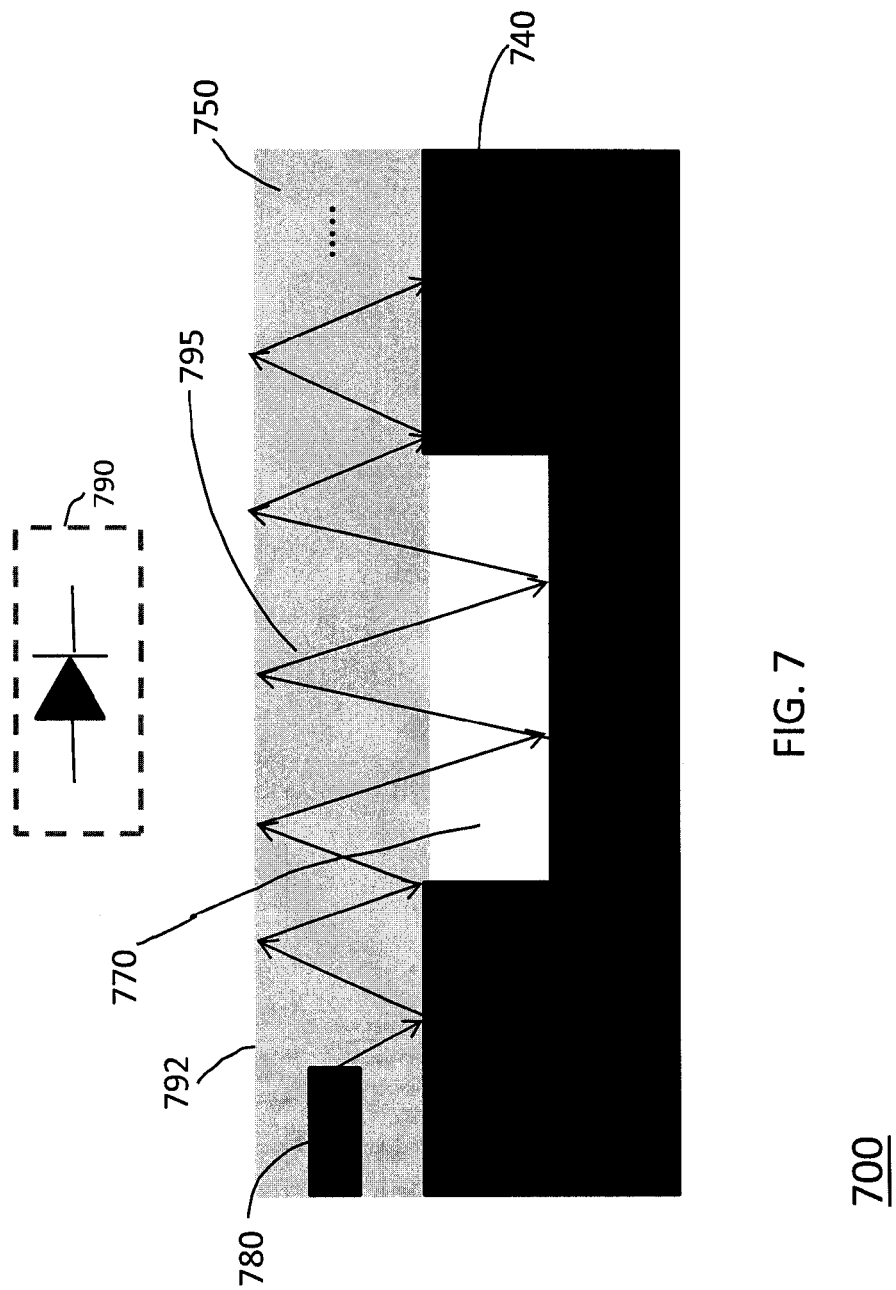
FIG. 7 shows a light propagation path within a microfluidic chamber.

FIG. 7 shows a PCR chamber (700) wherein light is emitted from a light source (780) and light reflections are represented by arrows (795). As shown in FIG. 7, light is guided within the PCR chamber (700) and light scattering is avoided by reflection from a substrate (740), made for example of a metal, and total internal reflection from the air interface (792). This wave-guiding enables an efficient interaction of the light with a PCR mixture sample within the microfluidic reservoir (770). It also enables minimal interference of the light with the fluorescence photo-detector (790), located above the PCR chamber (700). According to an embodiment of the present disclosure, the fluorescence photo-detector (790) is filtered to exclude the light emitted by the light source (780) from a fluorescence signal which is captured from the PCR chamber (700) during PCR operation.

Further referring to FIG. 6, the person skilled in the art will appreciate that through a use of available and cost-effective components, by integrating thermal cycling and optical excitation and eliminating a use of large multiwall plates as involved in conventional PCR systems, cost reduction will result in. As an example, applicants found that by integrating thin-film resistive heating sources, heating rates of over 50° C./s are possible. Also, a use of thin Ni—Cr, copper/nickel foil or graphite/polymer heaters enables heating and cooling to be performed without involving power-hungry Peltier junctions. In this way, overall power consumption is reduced. Moreover, referring to FIG. 6, applicants found that temperatures can be controlled to within 0.5° C. on-chip by standard feedback electronics, adequate to avoid primer-dimer amplification during the PCR cycling process. Primer-dimer is a pair of primers which anneal to each other instead of annealing to target DNA sequence (normally at 3' ends). This can be amplified by DNA polymerase enzyme. Since primers are normally in much greater excess, the amplicon can consume raw materials and also cause false fluorescent signal if fluorescent are being used With continued reference to the embodiment shown in FIG. 6, applicants demonstrated a thermal cycling, enabling 30 heating and cooling cycles between 55° C. and 95° C. within 65 seconds and DNA amplification (100 base pairs) within 95 seconds. Referring to the embodiment shown in FIG. 6, a speed of PCR amplification is currently limited not by thermal cycling speed but by the enzyme reaction time to re-constitute double-stranded DNA. Distinctly from conventional PCR systems, the embodiment shown in FIG. 7 is optimized for larger volumes found in clinical samples. As an example, moving of samples is avoided during PCR to ensure thermal control of 5-20 micro-liter sample volumes.

Figure 8:
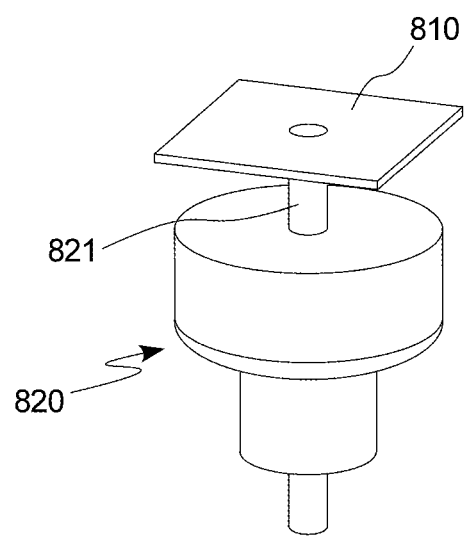
FIG. 8 shows a metal plate connected with a solenoid.

FIG. 8 shows a three-dimensional view of an implementation of the moving system (425) of FIGS. 4A-B in accordance with an embodiment of the present disclosure. A solenoid (820) is shown in FIG. 8. The solenoid (820) is connected with a plate (810) through a solenoid moving bar (821). According to an embodiment of the disclosure, the plate (810) serves as a metal thermal mass.

Referring to FIG. 8, a combination of the solenoid (820) and the plate (810) can be used in a microfluidic thermal cycling system. During a cycle, when the solenoid (820) is in a first state, the solenoid moving bar (821) moves the plate (810) to a first position wherein a thermal connection is established between the plate (810) and a microfluidic chamber (not shown). During the same cycle, when the solenoid (820) is in a second state, the solenoid moving bar (821) moves the plate (810) to a second position wherein the thermal contact between the moving bar (821) and the microfluidic chamber (not shown) is absent.

Figure 9:
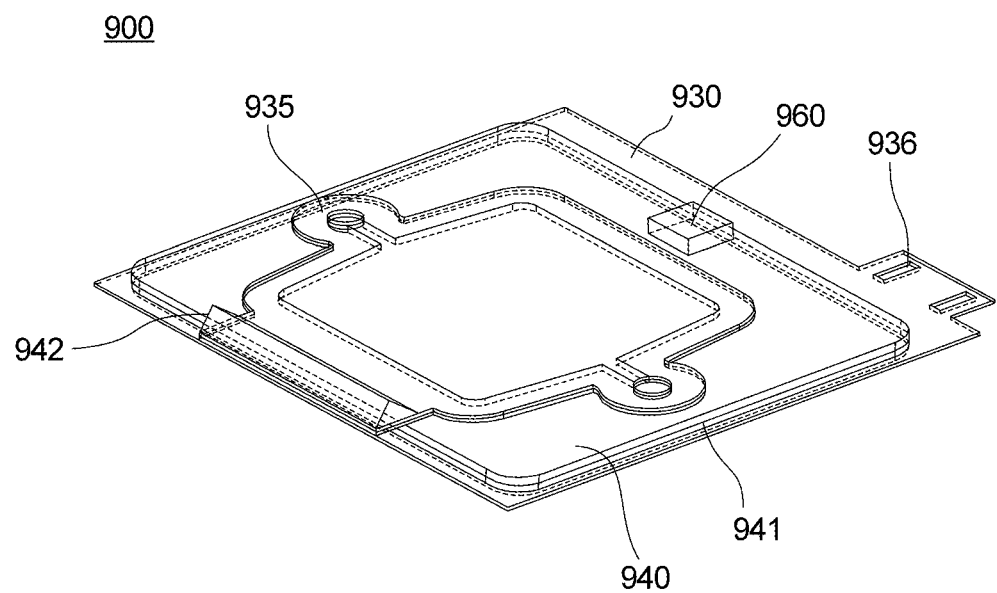
FIG. 9 shows a portion of a PCR system in accordance with an embodiment of the present disclosure.

In accordance with an embodiment of the present disclosure, FIG. 9 shows a microfluidic system (900) comprising a microfluidic reservoir (935), a substrate (940) and a heater (930) made of a PCB with electrodes (936) which provide current to turn the heater (930) on and off. The substrate (940) is electrically isolated from the heater (930) using an insulating layer (941). The microfluidic system (900) further comprises a prism (942) used for optical coupling purposes and a temperature sensor (960). Referring to FIG. 8, the person skilled in the art will understand that embodiments could be made where the heater (930), the temperature sensor (960) and the prism (942) are separate and not part of the microfluidic system (900). As an example, non-contact temperature sensing could be used (e.g., infrared).

Further referring to FIG. 8, the person skilled in the art will understand that a PCR system can be built using a combination of the microfluidic system (900) with the solenoid (820) and the plate (810) of FIG. 8. The person skilled in the art will also appreciate that such a PCR system combined with optical excitation/detection schemes can be used to provide a complete qPCR system. Examples of such combination are provided in below.

Figure 10A:
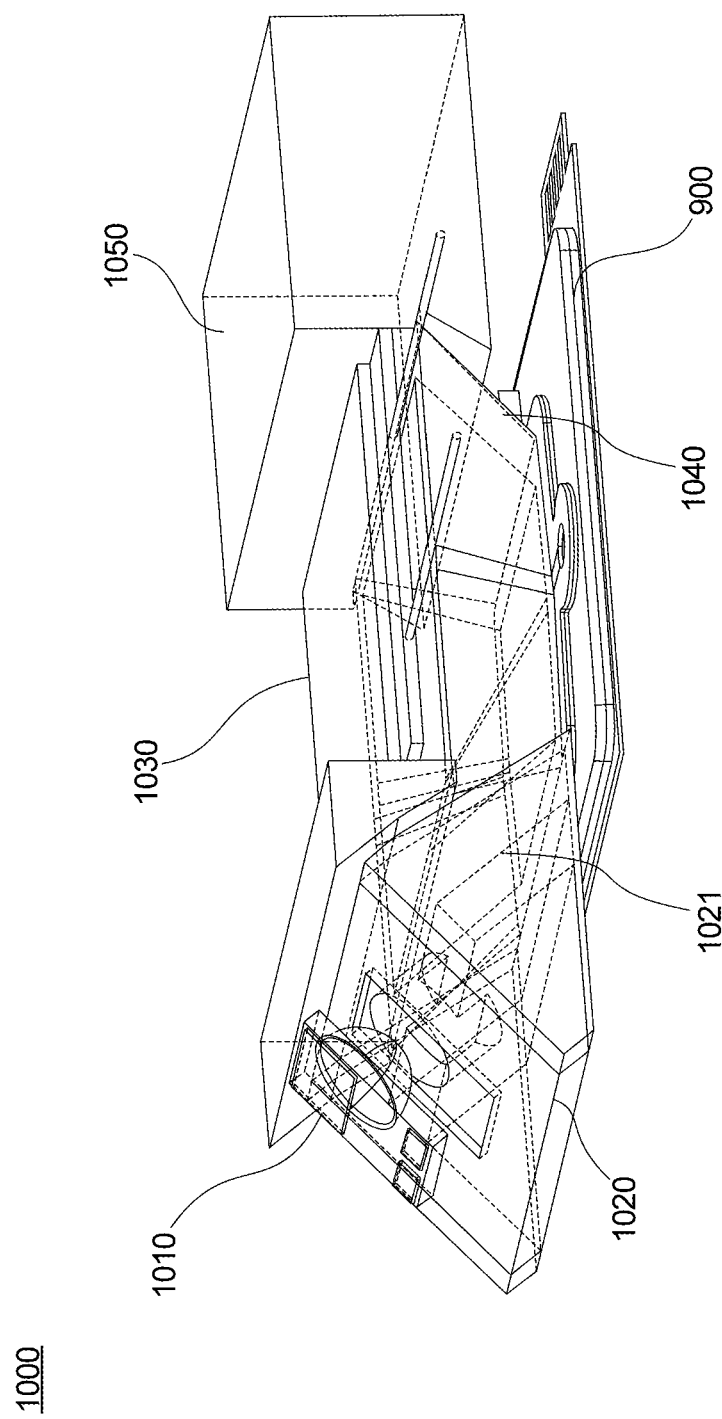
FIG. 10A shows a portion of a qPCR system in accordance with an embodiment of the present disclosure.

FIG. 10A shows a PCR device (1000) comprising the microfluidic system (900) of FIG. 9, a light source (1010), an optical emission assembly (1020), a light guide structure (1021), an optical detection assembly (1030) and a stray light reducer (1040) in accordance with an embodiment of the present disclosure. The light source (1010) generates an incident light which is guided through the optical emission assembly (1020) and then coupled into the microfluidic system (900) through the prism (942) shown in FIG. 9. A fluorescent light generated through an interaction between the incident light and a liquid sample within the microfluidic system (900) will be detected by the optical detection assembly (1030).

Referring to FIG. 10, according to an embodiment of the disclosure, the optical detection assembly (1030) comprises a photo-detector and an optical detection filter (not shown). The fluorescent light is at a longer wavelength than the incident light and as such, the optical detection filter is designed in a manner to filter out wavelength ranges non-overlapping with the fluorescent light wavelength. In this way, an amount of incident light from the light source (1010) reaching the optical detection assembly (1030) is reduced. Further reduction of the detected incident light from the light source (1010) by the optical detection assembly (1030) is ensured by the stray light reducer (1040). Moreover, the stray light reducer (1040) is so designed to maximize an amount of the incident light captured by a fluid within the microfluidic reservoir (935) shown in FIG. 9. A mechanical part (1050) is also shown in FIG. 10A. The mechanical part (1050) serves for mechanical attachment purposes as described later.

Figure 10B:
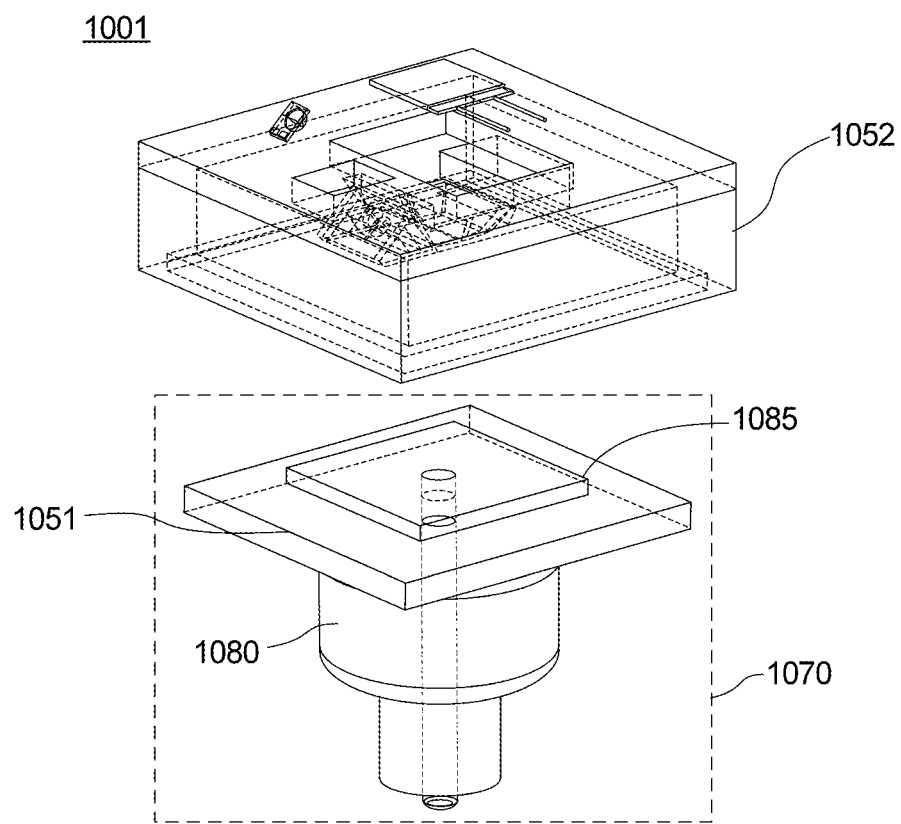
FIG. 10B shows a qPCR system in accordance with an embodiment of the disclosure.

FIG. 10B shows a qPCR system (1001) in accordance with an embodiment of the present disclosure. The qPCR system (1001) comprises a moving system (1070) and a casing (1052). The moving system (1070) further comprises a solenoid (1080), a thermal storage (1051) and a plate (1085). The thermal storage (1051) is a larger thermal mass than the plate (1085).

Referring to FIG. 10B, the casing (1052) comprises the PCR device (1000) of FIG. 10A. As mentioned previously, the mechanical part (1050) shown in FIG. 10A is served to attach and hold in place the PCR device (1000) of FIG. 10A within the casing (1052). Thermal cycling is performed in substantially similar way as described with reference to FIG. 8. In a state where there is no thermal connection between the casing (1052) and the moving system (1070), the plate (1085) is in thermal contact with the thermal storage (1051) and as a result, the temperature of the plate (1085) is reduced towards a temperature of the thermal storage (1051). Embodiments can be envisaged where the thermal storage (1051) can have fins (not shown) for a faster dissipation of heat to surroundings, water channels, ice containers etc.

Different variations of the embodiments shown in FIGS. 10A-B can be envisaged. As an example, optical measurements based on fluorescence or absorbance is possible. For fluorescent imaging, an optical excitation can be produced using an LED or a lamp providing an incident light within a desired wavelength range. According to an embodiment of the present disclosure, the incident light is filtered using an emission filter (not shown) which is served to block an incident light having wavelengths beyond the desired wavelength. According to a further embodiment of the present disclosure, in order to achieve a better coupling of the incident light, a collimator is used as part of the optical emission assembly (1020). Other embodiments of the present disclosure can be envisaged where an absorbance or a thin film filter is used as part of the optical detection assembly (1030).

FIG. 11A shows a multiple PCR reaction based system (1100). The multiple PCR reaction based system (1100) comprises a moving system (1409), a chip (1408), a micro array assembly (1405) and an optical assembly (1410). The moving system (1409) further comprises a solenoid (1411) and a plate (1412) and its function is substantially similar to the embodiments shown in FIG. 10B and FIG. 8. The optical assembly (1410) comprises elements (not shown) for light emission and fluorescence detection.

Referring to FIG. 11A the chip (1408) comprises a temperature sensor (1404), a metal substrate (1403) and an insulation layer (1402) insulating electrically the metal substrate (1403) from a heater (1401).

Further referring to FIG. 11A, the multiple PCR reaction based system (1100) also comprises a micro array element (1405). The micro array element (1405) comprises, in turn, a plurality of wells (1406). Differently from the qPCR systems (600A, 1001) of FIG. 6A and FIG. 10B, the multiple PCR reaction based system (1100) handles various PCR samples at the same time. In other words, the wells (1406) contain different PCR samples from various sources which can be processed simultaneously.

FIG. 11B shows a microarray (1451) as an implementation of the microarray (1405) of FIG. 11A. The microarray (1451) comprises a plurality of wells.

The present disclosure has shown temperature control devices and methods. While the temperature control devices and methods have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

The invention claimed is:

1. A temperature control method comprising:
providing an object of interest at a first temperature, the object of interest coupled to a first non-fluidic thermal path;
providing a thermal mass at a second temperature, the thermal mass coupled to a second non-fluidic thermal path;
using a thermoelectric heater/cooler for setting the thermal mass at the second temperature;
providing a thermal contact having a first position and a second position, the first position selected to accommodate a thermal transfer between the object of interest and the thermal mass through the first and second non-fluidic thermal paths;
setting the thermal contact to the first position;
establishing a desired temperature between the first temperature and the second temperature; and
setting the thermal contact to the second position when the object of interest reaches the desired temperature;
wherein the thermal contact comprises a liquid metal filled syringe, wherein the setting the thermal contact to the first position is set by pushing a syringe plunger, and the setting the thermal contact to the second position is set by pulling the syringe plunger.

2. The temperature control method of claim 1, further comprising controlling the position of the thermal contact by a feedback control system, the feedback control system comprising electronic circuits and a temperature sensor estimating a temperature of the object of interest.

3. The temperature control method of claim 1, further comprising controlling the rate of the thermal transfer by coating contact areas.

4. The temperature control method of claim 3, wherein coating contact areas comprises using at least one of a carbon nano-tube, flexible graphite, mercury, metal foil, or gallium.

5. The temperature control method of claim 1, wherein the separation distance is a variable separation distance that provides for a plurality of thermal transfer rates based on a corresponding plurality of separation distances.

6. The temperature control method of claim 1, wherein the thermoelectric heater/cooler for setting the thermal mass at the second temperature does not undergo temperature cycling.

7. A temperature cycling method comprising:
providing an object of interest;
providing a hot thermal mass at a first temperature $T_1$;
using a thermoelectric heater/cooler for setting the hot thermal mass at the first temperature $T_1$;
providing a cold thermal mass at a second temperature $T_2$;
using a thermoelectric heater/cooler for setting the cold thermal mass at the second temperature $T_2$;
providing a thermal contact having a first position and a second position;
during a cycle, establishing a non-fluidic thermal connection between the object of interest and the first thermal mass by positioning the thermal contact into the first position;
maintaining the thermal contact in the first position until the object of interest reaches a first desired temperature $T_{hot}$ that is located between the first temperature $T_1$ and the second temperature $T_2$; and
maintaining the thermal contact in the second position until the object of interest reaches a second desired temperature $T_{cold}$ that is located between the first temperature $T_1$ and the second temperature $T_2$;

wherein the thermal contact comprises a liquid metal filled syringe, wherein the setting the thermal contact to the first position is set by pushing a syringe plunger, and the setting the thermal contact to the second position is set by pulling the syringe plunger.

8. The temperature cycling method of claim 7, further comprising controlling the position of the thermal contact by a feedback control system, the feedback control system comprising electronic circuits and a temperature sensor measuring a temperature of the object of interest.

9. The temperature cycling method of claim 7, wherein the thermal contact is along a non-fluidic thermal path separate from the object of interest, the first thermal mass, and the second thermal mass.

10. The temperature control method of claim 9, wherein a distance of the non-fluidic thermal path is independent of the first position and the second position of the thermal contact.

11. The temperature cycling method of claim 7, further comprising controlling a heat transfer rate by coating contact areas.

12. The temperature cycling method of claim 11, wherein the coating is at least one of: carbon nano-tube, flexible graphite, mercury, metal foil, or gallium.

13. The temperature cycling method of claim 7, wherein the first thermal mass is a container of liquid having a temperature greater than a temperature of the object of interest, and the second thermal mass is a container of liquid having a temperature less than the temperature of the object of interest.

14. The temperature cycling method of claim 7, wherein the cold thermal mass at a second temperature $T_2$ comprises a first container containing ice.

15. The temperature cycling method of claim 14, wherein the hot thermal mass at a second temperature $T_1$ comprises a second container containing water.

16. The temperature cycling method claim 7, wherein the thermoelectric heater/cooler for setting the hot thermal mass at the first temperature $T_1$ and the thermoelectric heater/cooler for setting the cold thermal mass at the second temperature $T_2$ do not undergo temperature cycling.

* * * * *